United States Patent
Pan et al.

(10) Patent No.: US 7,804,070 B1
(45) Date of Patent: Sep. 28, 2010

(54) SCANNING DEVICE OF MULTI-POINT SIMULTANEOUS ACQUISITION THROUGH DIFFUSE OPTICAL TOMOGRAPHY

(75) Inventors: Min-Chun Pan, Ping-Jen (TW); Chien-Hung Chen, Meinan Village (TW); Min-Cheng Pan, Keelung (TW)

(73) Assignee: National Central University, Taoyuan (TW)

( * ) Notice: Subject to any disclaimer, the term of this patent is extended or adjusted under 35 U.S.C. 154(b) by 0 days.

(21) Appl. No.: 12/076,251

(22) Filed: Mar. 14, 2008

(30) Foreign Application Priority Data

Nov. 8, 2008  (TW) .................................. 096142162

(51) Int. Cl.
*G01N 21/49* (2006.01)
(52) U.S. Cl. ..................................... 250/341.1; 600/425
(58) Field of Classification Search ................. 600/425; 250/341.1

See application file for complete search history.

(56) References Cited

FOREIGN PATENT DOCUMENTS

WO  WO 9920997 A1 *  4/1999

OTHER PUBLICATIONS

Min-Chun Pan et al., "Development and System Characteristics of Diffuse Optical Tomography Using Single Rotating-Source/Detector Mechanism." Advanced Biomedical and Clinical Diagnostic Systems IV, Proc. of SPIE vol. 6080, 60800D (2006) 8 pages <doi: 10.1117/12.645044>.*

* cited by examiner

*Primary Examiner*—Constantine Hannaher
(74) *Attorney, Agent, or Firm*—Jackson IPG PLLC; Demian K. Jackson

(57) ABSTRACT

A scanning device processes a multi-point simultaneous acquisition. The acquisition is processed for an infra-red diffuse optical tomography. An intensity modulated light is used with a frequency domain analysis theorem to obtain a reconstructed scanning image. The fibers are capable of a vertical movement and a radial movement. Thus, a precise image showing optical-information data is obtained with a low cost, even through scanning at a minimal angle.

19 Claims, 12 Drawing Sheets

SCANNING DEVICE OF MULTI-POINT SIMULTANEOUS ACQUISITION THROUGH DIFFUSE OPTICAL TOMOGRAPHY

FIELD OF THE INVENTION

The present invention relates to a scanning device; more particularly, relates to a device of a multi-point simultaneous acquisition through a near infra-red (NIR) diffuse optical tomography, where a reconstructed scanning image is obtained with a intensity modulated light through a frequency domain analysis theorem; and a vertical movement and a radial displacement for source/detector fibers are thus obtained with a big fiber scanning range.

DESCRIPTION OF THE RELATED ART

As incidence and mortality of breast cancer increase, a scanning device for early stage detection is urgently required. And, a technology of near infrared tomography is thus developed The device for scanning breast cancer through NIR diffuse optical tomography have source fibers and detecting fibers fixed on an O-shape holder, where each two of the source fibers and detecting fibers have an equal space in between for a multi-channel simultaneous acquisition; and a scanning along the object boundary is operated by switching among the fibers. However, because the detecting fibers have an equal angle setting, a minimal scanning is not available and data obtained is thus limited with limited number of detecting fibers. Hence, a reconstructed image obtained has a bad spatial resolution. For improving the spatial resolution of the tomography image, more detection elements along with detecting fibers are required for a simultaneous acquisition and so a high cost is resulted in. Moreover, the detection element has a certain size so that the spatial resolution of the tomography image is limited owing to a limited number of channels. Hence, the prior art does not fulfill all users' requests on actual use.

SUMMARY OF THE INVENTION

The main purpose of the present invention is to provide a scanning device of a multi-point simultaneous acquisition through a NIR diffuse optical tomography with a single light source, where an intensity modulated light is used to obtain a reconstructed scanning image through a frequency domain analysis theorem.

Another purpose of the present invention is to utilize fixed source/detector fibers on a C-shape holder capable of vertical and radial movements, where a multi-point simultaneous scanning with arbitrary stepping is processed with fewer source fibers, detecting fibers and detectors; and a precise image is figured out through a minimal scanning with a scanning time saved.

To achieve the above purposes, the present invention is a scanning device of a multi-point simultaneous acquisition through a diffuse optical tomography, comprising a vertical moving stage, an assistant vertical track, a vertical moving stage adapter, a rotating device, a rotational stage fastening plate, a radial movement control motor, a fiber holder and a source fiber holder, where the vertical moving stage is moved to a surface of a scanned object through a linear vertical movement along the assistant vertical track; detecting fibers process a simultaneous detecting after the source fiber is positioned; and the source fiber and the detecting fibers are simultaneously moved to a next angle with an equal speed after a round of scanning for the next round of detection; and where the fiber holder is drawn by an actuating wire to scale down a scanning radius with a radial control motor to contact the source fiber and the detecting fibers with a surface of a scanned object; the fiber holder is moved radially when the actuating wire is released for departing the source fiber and the detecting fibers from the surface of the scanned object; and the radius is scaled down again after a next angle is set for the next round of detection. Accordingly, a novel scanning device of a multi-point simultaneous acquisition through a diffuse optical tomography is obtained.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

Figure 1:
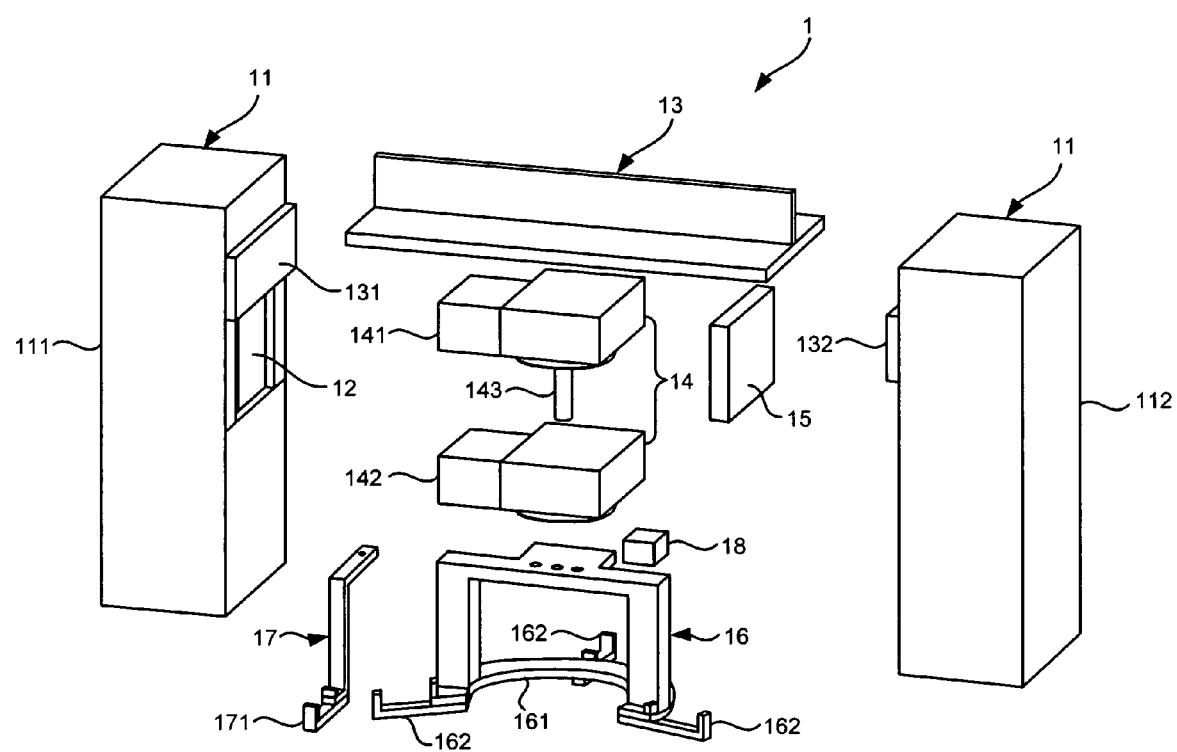
FIG. 1 is the sectional view showing the preferred embodiment according to the present invention.

The following description of the preferred embodiment is provided to understand the features and the structures of the present invention.

Please refer to FIG. 1 to FIG. 4, which are a sectional view showing a preferred embodiment according to the present invention; two views showing a radial movement control; and a perspective and a sectional views showing a fiber fastener. As shown in the figures, the present invention is a scanning device 1 of a multi-point simultaneous acquisition through a diffuse optical tomography, comprising a vertical moving stage 11, an assistant vertical track 12, a vertical moving stage adapter 13, a rotating device 14, a rotational stage fastening plate 15, a fiber holder 16, a source fiber holder 17 and a radial movement control motor 18.

The vertical moving stage 11 is deposed on a vertical displacing area, comprising a first moving stage 111 and a second moving stage 112.

The assistant vertical track 12 is located at inner sides of the first and the second moving stages 111,112.

The vertical moving stage adapter 13 is movably deposed on a first moving plate 131 and a second moving plate 132 to be connected with the first moving stage 111 and said second moving stage 112. And the first moving plate 131 and the second moving plate 132 are moved along the assistant vertical track 12 to a surface of a scanned object.

The rotating device 14 comprises a first rotating stage 141, a second rotating stage 142 and a rotating axis 143. The rotating device 14 is fixed at the same side of the first and the second rotating stages 141,142 with a rotational stage fastening plate 15. And the fiber holder 16 and the source fiber holder 17 have an equal-speed rotation on the scanned object by the rotating device 14. Therein, the first rotating stage 141 and the second rotating stage 142 have rotational angles of 108°, 80° and 64° separately for a three-point, a four-point and a five-point simultaneous acquisitions of the scanned object, where optimal scanning angles for a scanning device of a multi-point simultaneous acquisition is equally derived by deducting an interference dead-zone of the source fiber holder 17.

A C-shape holder 161 under the fiber holder 16 has a plurality of fiber fasteners 162. Each two of the neighboring fiber fasteners 162 have an equal space in between. The C-shape holder 161 has a plurality of connecting parts 163 at border. And each of the fiber fasteners 162 fastens a detecting fiber 3 with a fixing screw 21 underneath for the detecting fiber 3 to rotate along with the fiber fastener 162. Therein, the connecting part 163 is inlayed in a track 1621 of the fiber fastener 162 and the detecting fiber 3 is inserted in a fiber setting hole 1622. The fiber fastener 162 has a linear variable resistance 1623 (or other position sensor) and a front-end membrane-like pressure sensor 1624 (or other touch sensor). With the linear variable resistance 1623, a position is obtained through resistance changes along a radial displacement; and, with the front-end membrane-like pressure sensor 1624, a contact status on a surface of the scanned object is obtained. And an actuating wire hole 1631 is set above the connecting part 163.

The source fiber holder 17 is deposed on the fiber holder 16 along the rotating axis 143. The source fiber holder 17 has a source fiber fastener 171 underneath and a connecting part 172 at border. Beneath the source fiber fastener 171, a source fiber 4 is set with a fixing screw 22 for rotating. Thus, a scanning arm is obtained with the rotating device 14 and the fiber holder 16. Therein, the connecting part 172 is inlayed in a track 1711 with the source fiber fastener 171, and the source fiber 4 is inserted in a source fiber setting hole 1712. The source fiber fastener 171 has a linear variable resistance 1713 (or other position sensor) and a front-end membrane-like pressure sensor 1714 (or other touch sensor). A position is obtained by the linear variable resistance 1723 through resistance changes along a radial displacement; a contact status on a surface of the scanned object is detected by the membrane-like pressure sensor 1724; and, an actuating wire hole 1721 is set above the connecting part 172.

The radial movement control motor 18 is set on the fiber holder 16 for tuning a scanning radius of the scanned object by moving the source fiber fastener 171 and the fiber fastener 162 through a plurality of actuating wires 181. Therein, the actuating wire 181 passes through the actuating wire hole 1631,1731 above the connecting part 163,172; the actuating wire 181 is covered with a wire shell 182 before passing through the actuating wire hole 1631,1731; and, after the actuating wire 181 passes through the actuating wire hole 1631,1731, the actuating wire 181 is connected with a spring 183 and is fixed on a fiber fastener 162 with a fixing screw 23.

Figure 2A:
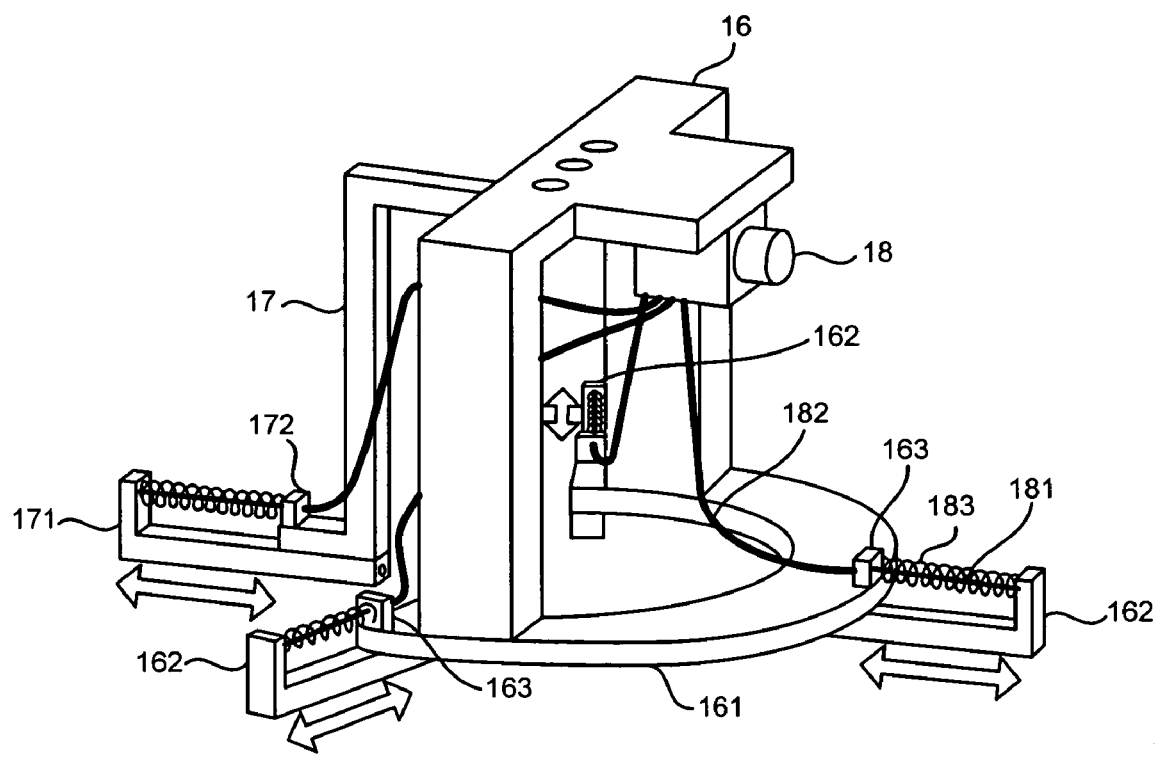
FIG. 2A is the view showing the radial movement control.
Figure 2B:
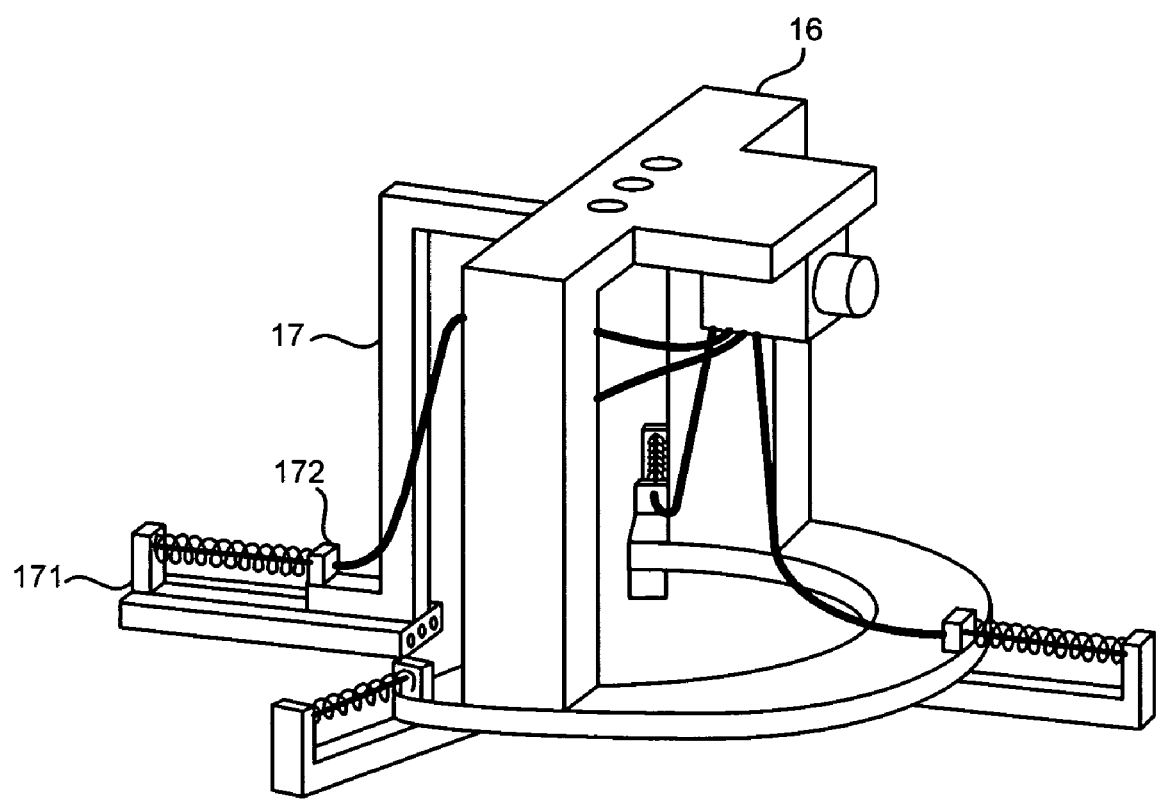
FIG. 2B is another view showing the radial movement control.
Figure 3:
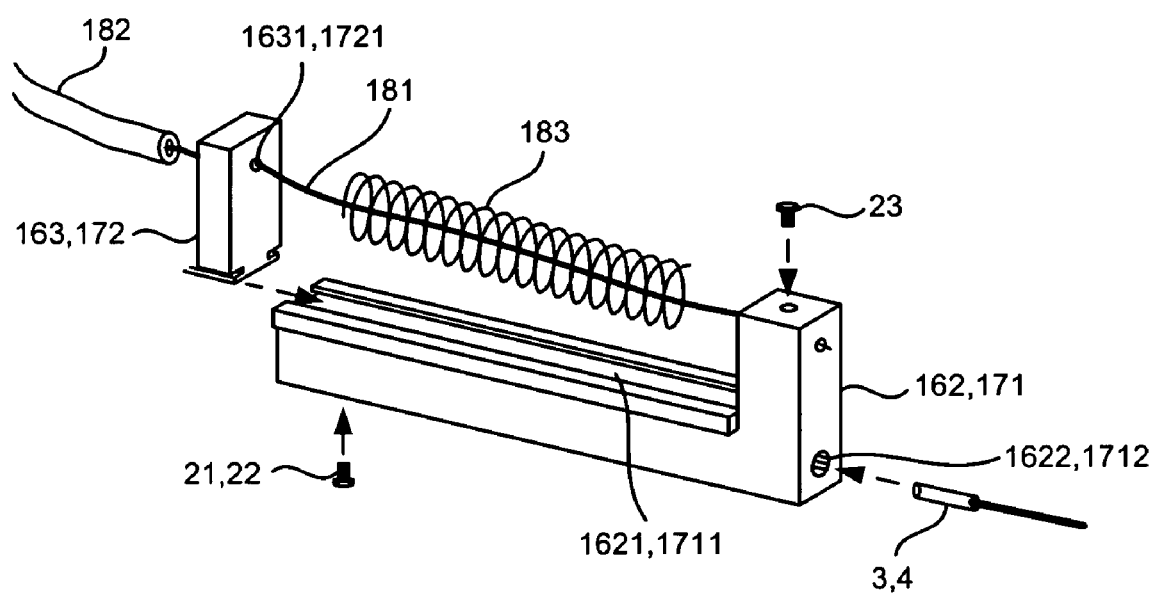
FIG. 3 is the perspective view showing the fiber fastener.
Figure 4:
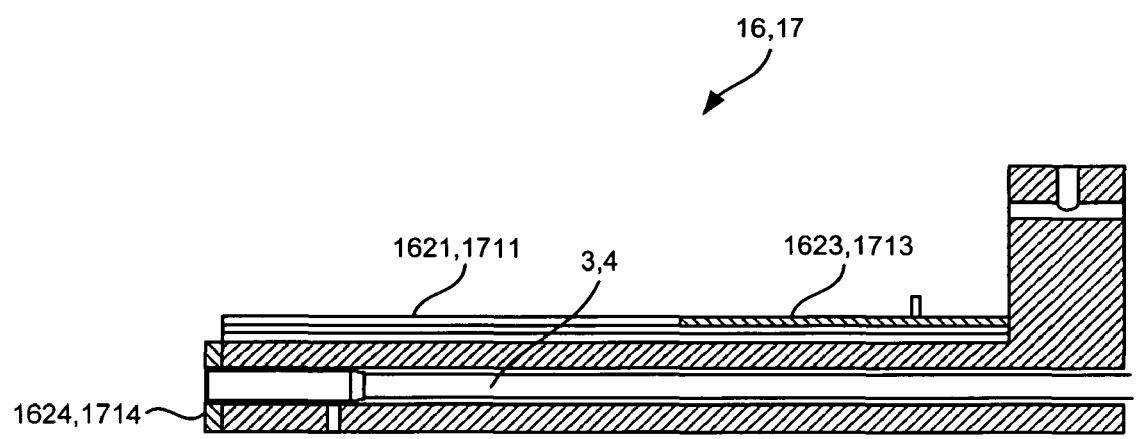
FIG. 4 is the sectional view showing the fiber fastener.
Figure 5:
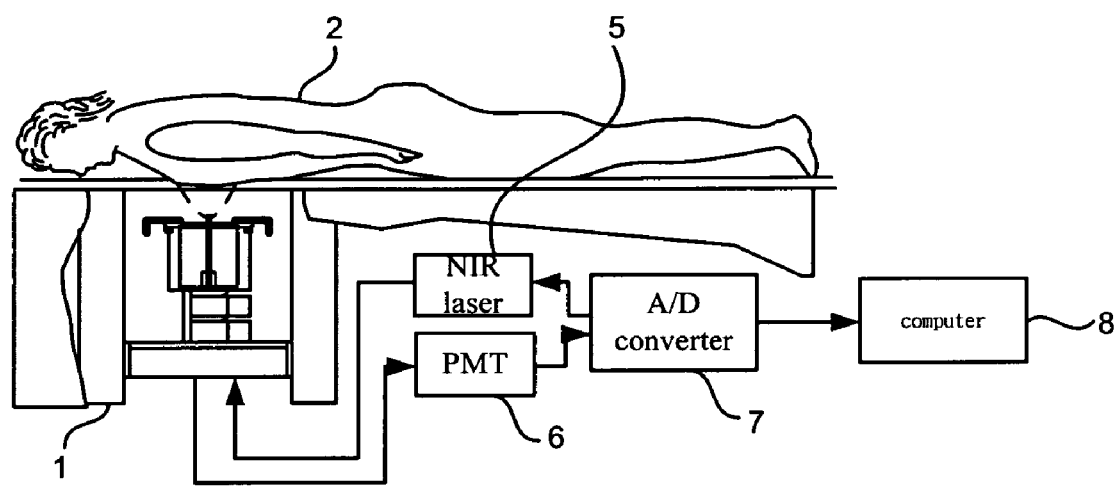
FIG. 5 is the view showing the breast cancer scanning.
Figure 6:
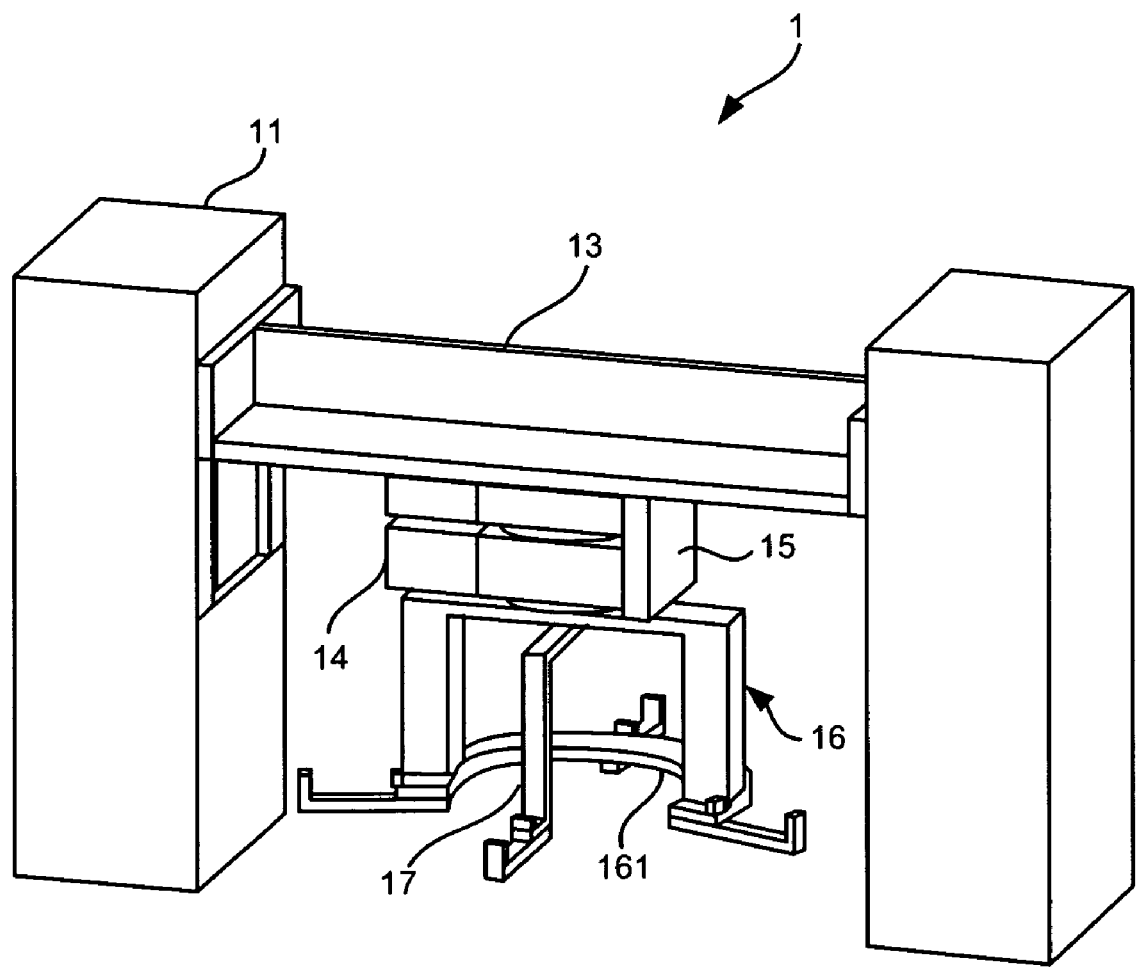
FIG. 6 is the perspective view showing the preferred embodiment.
Figure 7:
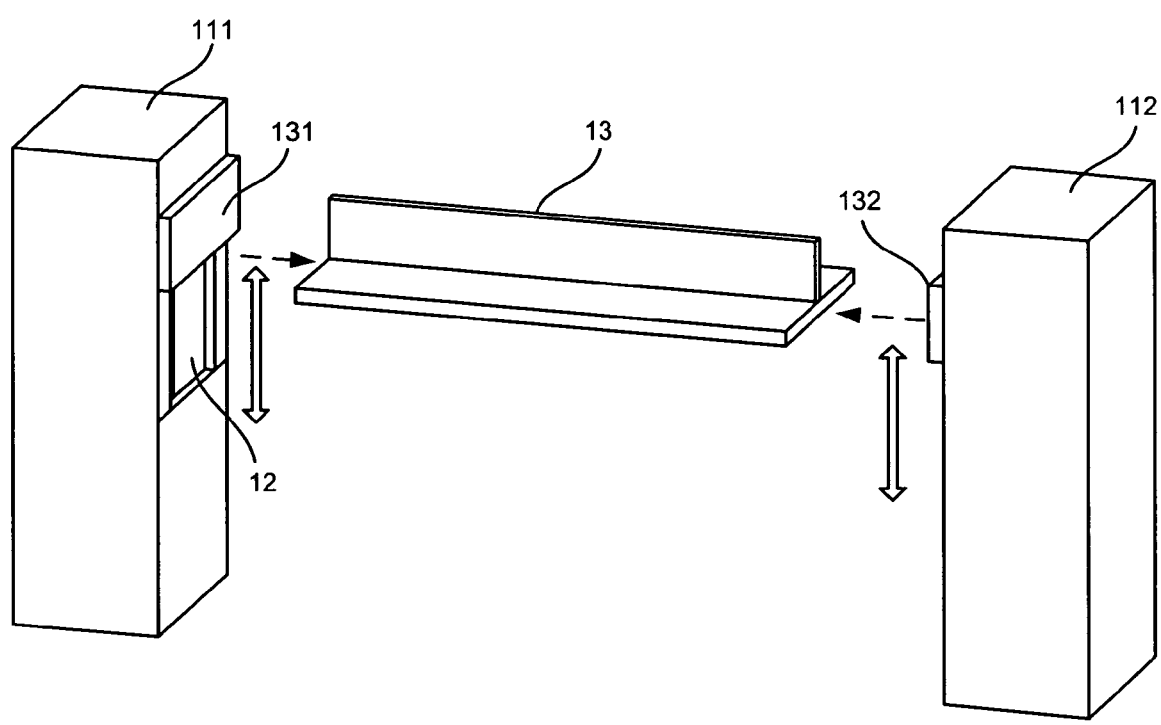
FIG. 7 is the view showing the vertical movement.

As shown in FIG. 2B, detecting fibers are set at two sides of the source fiber 4 to provide extra detecting data; and, the fiber holder shown in FIG. 2A and FIG. 2B can be replaced before scanning. Thus, a novel scanning device 1 according to the present invention is obtained.

Please refer to FIG. 5 to FIG. 9, which are a view showing a breast cancer scanning; a perspective view showing the preferred embodiment; views showing a vertical movement and a rotational movement; and a view showing angle of a three-point simultaneous scanning. As shown in the figures, a scanning device 1 according to the present invention is used in a breast cancer scanning system coordinated with a near infrared (NIR) laser 5, a photo multiplier tube (PMT) 6, an analog/digital (A/D) converter 7 and a computer 8. The scanning device 1 processes a NIR diffuse optical tomography with an intensity modulated light for a reconstructed scanning image through a frequency domain analysis theorem, where a C-shape holder 161 is used for a multi-point simultaneous acquisition.

Take a three-point simultaneous acquisition as an example. On using the present invention, a linear vertical movement is processed by a vertical moving stage 11. After a source fiber 4 of a NIR laser is positioned, the NIR laser is transilluminated on a surface of a scanned object 2 through three detecting fibers 3a,3b,3c. The three detecting fibers 3a,3b,3c have an equal space of 108° in between to output NIR radiance for a simultaneous detection. Each scanning range for the simultaneous detection is 108° and so total scanning range of 324° is obtained with the three detecting fibers 3a,3b,3c. After signals obtained by the detection are processed with an electro-optics transformation by the PMT 6 and the signal processor 7, an image reconstruction is processed by the computer 8. Hence, the present invention has a scanning speed faster than a single-point scanning system for three times. After a round of scanning, the three detecting fibers 3a,3b,3c are then simultaneously moved to a next angle with an equal speed for the next round of detection.

Furthermore, the present invention is able to process a scanning at a minimal angle. A radial movement control motor 18 is used to scale down a scanning radius for contacting the source fiber 4 and the detecting fibers 3a,3b,3c with a surface of the scanned object 2 by drawing a fiber holder 16 with an actuating wire. Then, when the actuating wire is released, the fiber holder 16 is moved outwardly by a spring for a radial displacement. Thus, the source fiber 4 and the detecting fibers 3a,3b,3c are moved outwardly for the radial displacement for departing from the surface of the scanned object 2. After a new angle is set and a repositioning at the new angle is done, the radius is scaled down again to contact the source fiber and the detecting fibers 3a,3b,3c with the surface of the scanned object 2. In this way, different sizes of scanned objects are detected, where not only deviations are reduced for a direct-contact acquisition, but also a rotating arm is scaled down in size when wire control is used.

Consequently, a stepping scanning for 324° at any minimal angle is processed with the three detecting fibers 3a,3b,3c to obtain more data for figuring out detail scanned image with a scanning time saved. The image obtained is thus precise coordinated with a radial displacement sensor; and is outlined on reconstructing the image. Conclusively, the present invention has source/detector fibers with a vertical movement and a radial displacement, where numbers of source fibers, detecting fibers and detectors are reduced with low cost; and a precise scanning at a minimal angle is done with the present invention.

Figure 8:
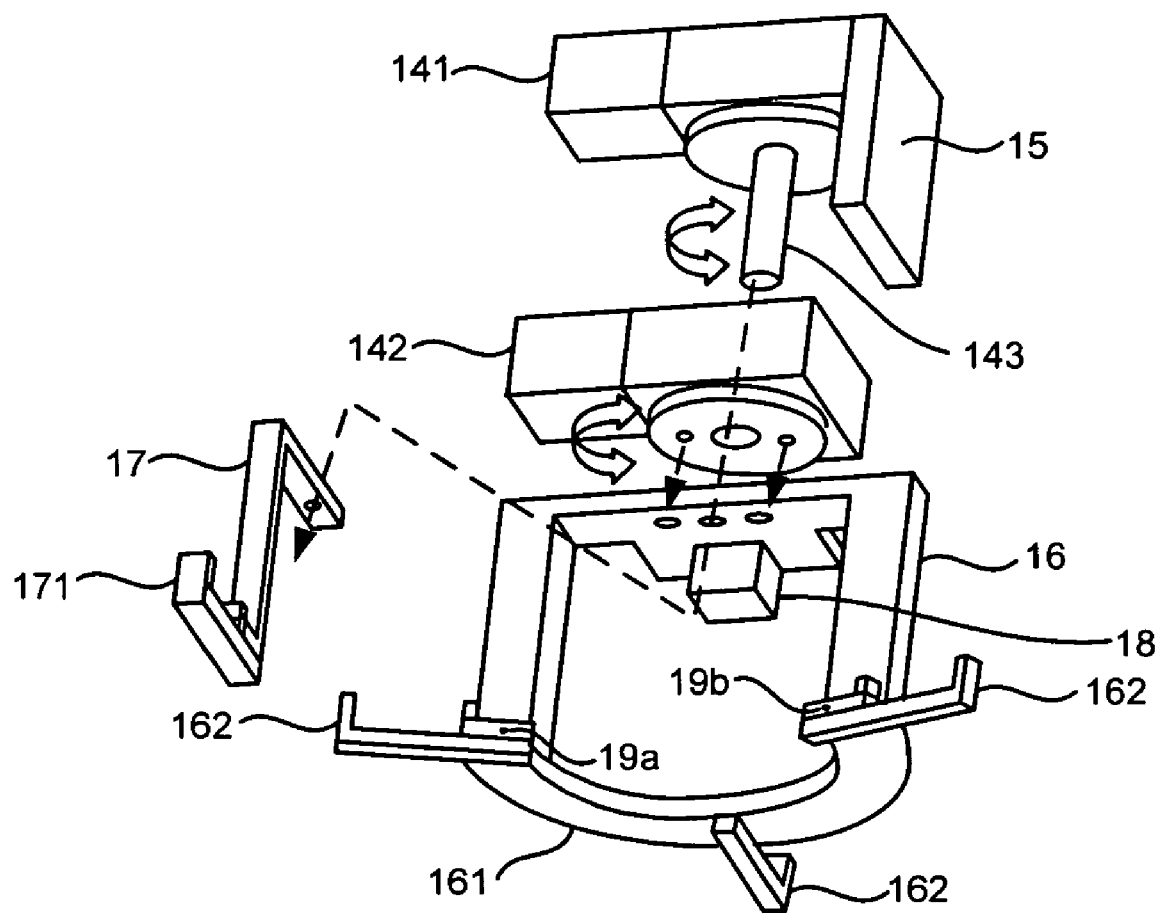
FIG. 8 is the view showing the rotational movement.
Figure 9:
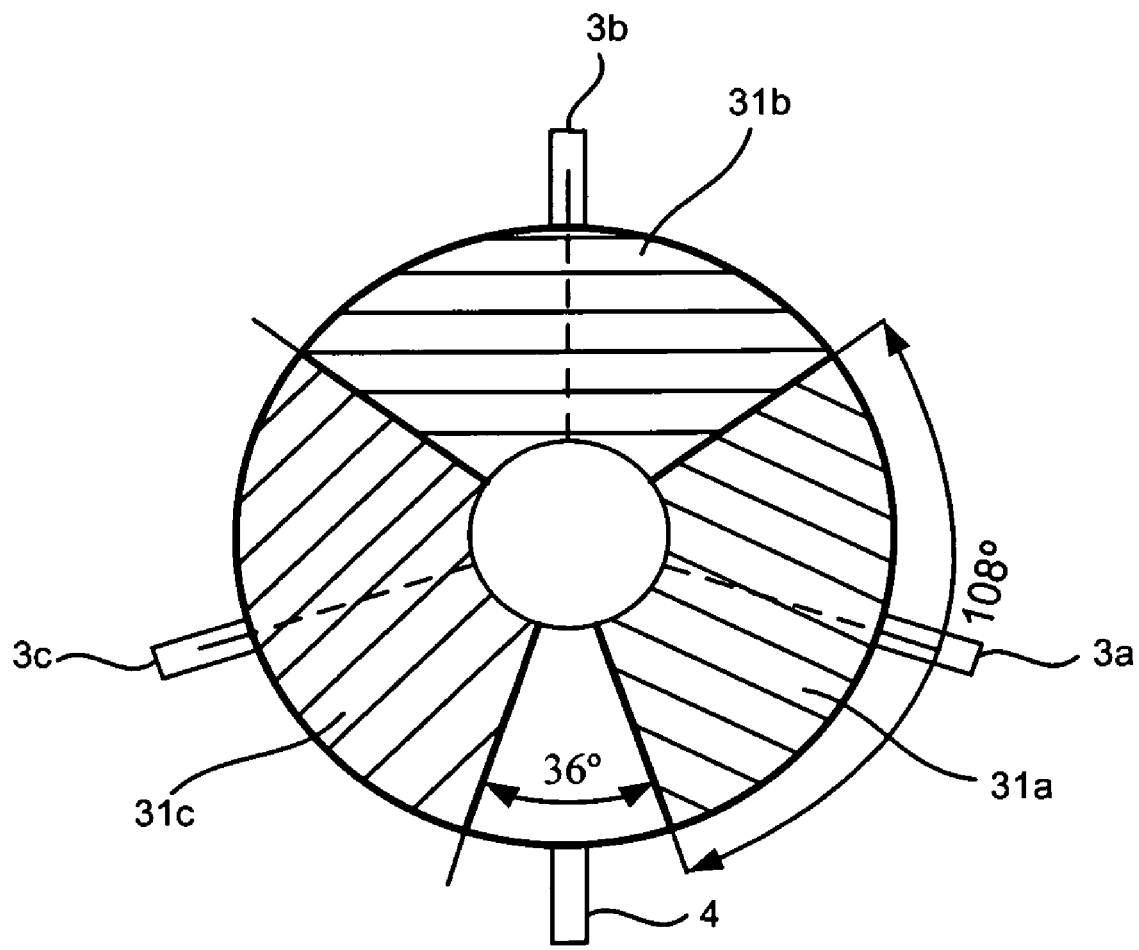
FIG. 9 is the view showing the angle of the three-point simultaneous scanning.

As shown in FIG. 8, a C-shape holder 161 has touch sensors 19a,19b at two sides to prevent a scanning arm from touching the C-shape holder 161, and thus the scanning does not stop eventually or even corrupting the system.

Figure 10:
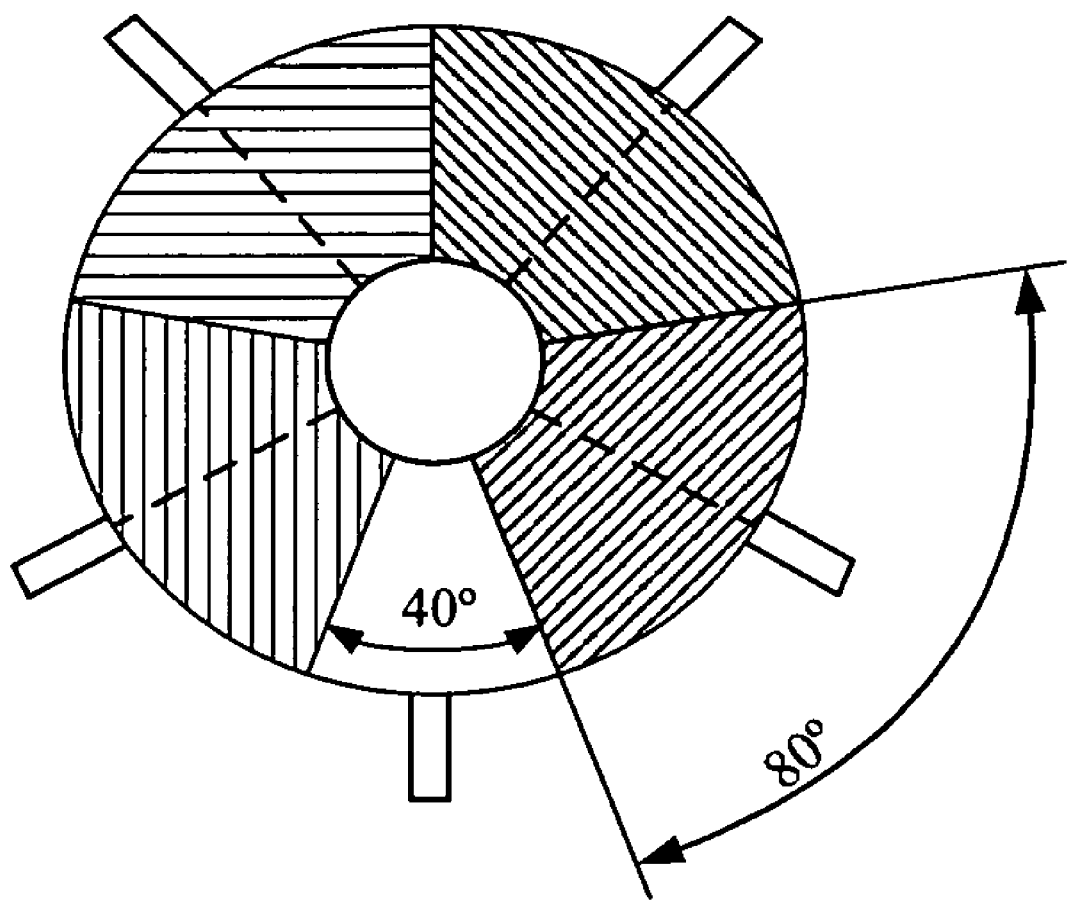
FIG. 10 is the view showing the angle of the four-point simultaneous scanning.
Figure 11:
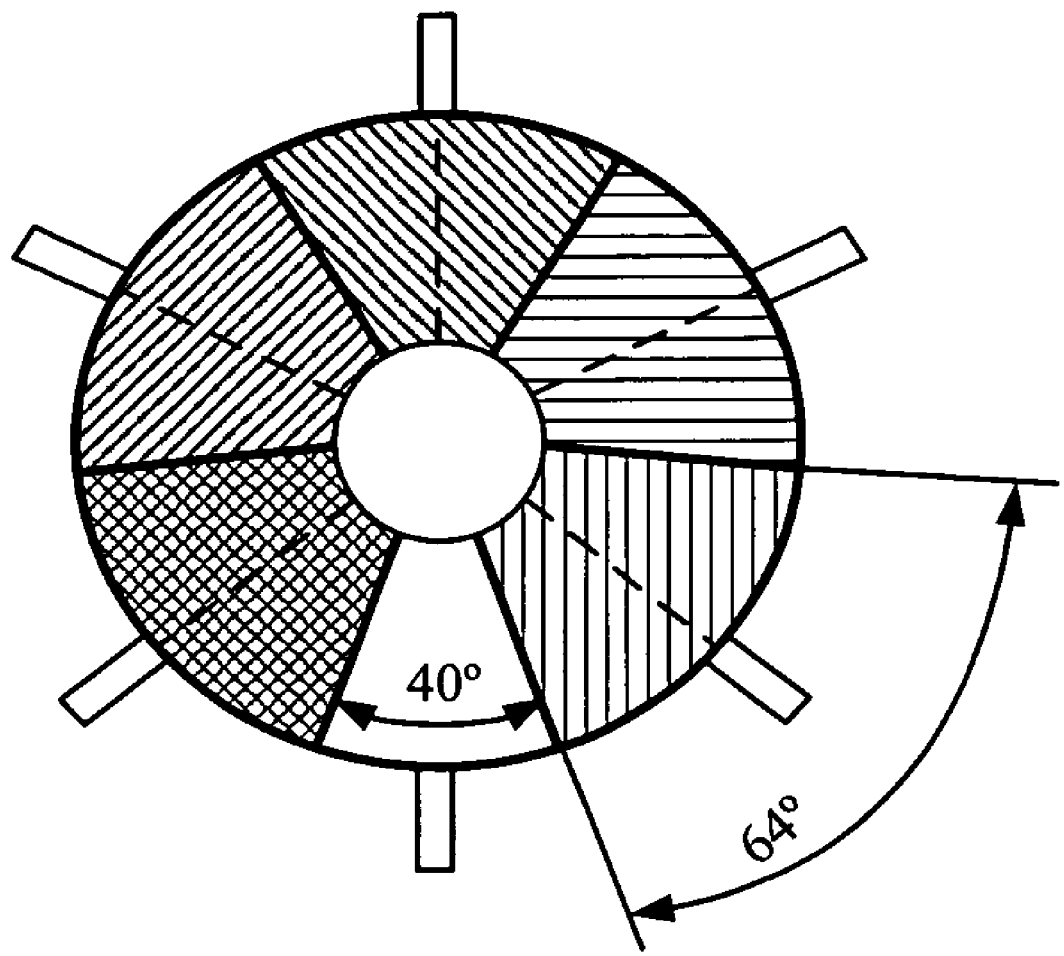
FIG. 11 is the view showing the angle of the five-point simultaneous scanning.

Please refer to FIG. 10 and FIG. 11, which are views showing angles of a four-point simultaneous scanning and a five-point simultaneous scanning. As shown in the figures, a scanning device for a diffuse optical tomography processes a four-point simultaneous acquisition and a five-point simultaneous acquisition. Therein, each fiber on a C-shape holder have a scanning range of 80° and 64° at each scanning point for the four-point simultaneous acquisition and the five-point simultaneous acquisition respectively to obtain a total scanning range of 320°. And simultaneous acquisitions for more than five points can be obtained in the like way. Hence, only source fibers and detecting fibers are needed to be added on a scanning arm for a multi-point simultaneous acquisition with a single light source, where the single light source is deposed on a fastening arm of a single source fiber. In practice, the single light source can be a multiple-input single-output fiber, where lasers with various wavelengths are modulated with various frequencies to enter into a fiber for identifying more tissue optical properties. In a word, more time can be saved by using the multiple-input single-output fiber than using a wavelength tunable laser or a light transmitting path switch.

To sum up, the present invention is a scanning device of a multi-point simultaneous acquisition through a diffuse optical tomography, where the scanning device is a single light source of a multi-point simultaneous acquisition through a NIR diffuse optical tomography to obtain a reconstructed scanning image with a intensity modulated light through a frequency domain analysis theorem; C-shape fiber holders is used with source/detector fibers having a vertical and a radial movements in the multi-point simultaneous acquisition that numbers of source fibers, detecting fibers and detectors are reduced with low cost and precise scanning at minimal angle is done.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A scanning device of a multi-point simultaneous acquisition through a diffuse optical tomography, comprising:
    a vertical moving stage, said vertical moving stage being deposed on a vertical displacing area, said vertical moving stage comprising a first moving stage and a second moving stage;
    an assistant vertical track, said assistant vertical track being located at opposing sides of said first moving stage and said second moving stage;
    a vertical moving stage adapter, said vertical moving stage adapter being movably deposed on a first moving plate of said first moving stage and a second moving plate of said second moving stage, said vertical moving stage adapter connecting to said first moving stage and said second moving stage, said first moving plate and said second moving plate moving along said assistant vertical track to a surface of a scanned object;
    a rotating device, said rotating device comprising a first rotating stage, a second rotating stage and a rotating axis, said rotating device rotating on said scanned object;
    a rotational stage fastening plate, said rotational stage fastening plate being deposed at a side of said first moving stage and said second moving stage, said rotational stage fastening plate fastening said rotating device;
    a fiber holder, said fiber holder having a C-shape holder at a side, said C-shape holder having a plurality of fiber fasteners, said fiber fastener fastening a detecting fiber, said detecting fiber rotating along said fiber fastener;
    a source fiber holder, said source fiber holder being deposed on said fiber holder along said rotating axis, said source fiber holder having a source fiber fastener at a side, said source fiber fastener fastening a source fiber, said source fiber rotating along said source fiber fastener; and
    a radial movement control motor, said radial movement control motor being deposed on said fiber holder, said radial movement control motor tuning a scanning radius of said scanned object by moving said source fiber fastener and said fiber fasteners through a plurality of actuating wires.

2. The scanning device according to claim 1,
    wherein said scanning device has a single light source to process a multi-point simultaneous acquisition.

3. The scanning device according to claim 1,
    wherein said fiber fastener has a track and a fiber setting hole; and
    wherein said fiber fastener has a position sensor and has a touch sensor at an end.

4. The scanning device according to claim 3,
    wherein said position sensor is a linear variable resistance; and
    wherein said touch sensor is a membrane-like pressure sensor.

5. The scanning device according to claim 1,
    wherein said C-shape holder has a plurality of connecting parts to be inlayed into a plurality of tracks separately at border of said C-shape holder.

6. The scanning device according to claim 5,
    wherein said connecting part has an actuating wire hole; and
    wherein an actuating wire passes through said actuating wire hole.

7. The scanning device according to claim 6,
    wherein said actuating wire is covered with a wire shell before passing through said actuating wire hole.

8. The scanning device according to claim 6,
    wherein, after said actuating wire passes through said actuating wire hole, said actuating wire is connected with a spring and is fixed on a fiber fastener with a fixing screw.

9. The scanning device according to claim 1,
    wherein said detecting fiber is deposed at a side of said fiber fastener with a fixing screw holder.

10. The scanning device according to claim 1,
    wherein said fiber fastener is deposed at a side of said fiber holder; and
    wherein each two neighboring fiber fasteners have an equal space in between.

11. The scanning device according to claim 1,
    wherein said source fiber fastener has a track and a source fiber setting hole; and
    wherein said source fiber fastener has a position sensor and has a touch sensor at an end.

12. The scanning device according to claim 11,
    wherein said position sensor is a linear variable resistance; and
    wherein said touch sensor is a membrane-like pressure sensor.

13. The scanning device according to claim 1,
    wherein said source fiber holder has a connecting part at a side to be inlayed into a track.

14. The scanning device according to claim 13,
    wherein said connecting part has an actuating wire hole; and
    wherein an actuating wire passes through said actuating wire hole.

15. The scanning device according to claim 14,
    wherein said actuating wire is covered with a wire shell before passing through said actuating wire hole.

16. The scanning device according to claim 14,
wherein, after said actuating wire passes through said actuating wire hole, said actuating wire is connected with a spring and is fixed on a source fiber fastener with a fixing screw.

17. The scanning device according to claim 1,
wherein said source fiber is deposed at a side of said source fiber fastener with a fixing screw holder.

18. The scanning device according to claim 1,
wherein said first rotating stage and said second rotating stage have an equal-speed rotation.

19. The scanning device according to claim 1,
wherein said first rotating stage and said second rotating stage have a rotational angle of 108° for a three-point simultaneous acquisition of said scanned object;
wherein said first rotating stage and said second rotating stage have a rotational angle of 80° for a four-point simultaneous acquisition of said scanned object; and
wherein said first rotating stage and said second rotating stage have a rotational angle of 64° for a five-point simultaneous acquisition of said scanned object.

\* \* \* \* \*